United States Patent [19]

Poos

[11] 3,959,479
[45] May 25, 1976

[54] ANTI-ANGINAL ACTIVITY OF 2-ARALKYLIMINO-AZEPINES

[75] Inventor: George Ireland Poos, Ambler, Pa.

[73] Assignee: McNeil Laboratories, Inc., Fort Washington, Pa.

[22] Filed: Apr. 26, 1974

[21] Appl. No.: 464,404

Related U.S. Application Data

[60] Continuation-in-part of Ser. No. 253,711, May 16, 1972, abandoned, which is a continuation-in-part of Ser. No. 85,733, Oct. 30, 1970, abandoned, which is a division of Ser. No. 738,379, June 17, 1968, abandoned, which is a continuation-in-part of Ser. No. 649,812, June 29, 1967, abandoned, which is a continuation-in-part of Ser. No. 409,563, Nov. 6, 1964, abandoned.

[52] U.S. Cl. .................................. 424/282; 424/244
[51] Int. Cl. ..................... A61k 33/32; A61k 31/36
[58] Field of Search ............................ 424/282, 244

[56] References Cited
UNITED STATES PATENTS 3,378,438  4/1968  Gatzi .................................. 424/282

*Primary Examiner*—Sam Rosen
*Assistant Examiner*—Daren M. Stephens

[57] ABSTRACT

Anti-anginal activity of certain 2-aralkylimino-hexahydro-1-$R_1$-2$\underline{H}$-azepines and pharmaceutical compositions thereof.

22 Claims, No Drawings

ANTI-ANGINAL ACTIVITY OF 2-ARALKYLIMINO-AZEPINES

CROSS-REFERENCE TO RELATED APPLICATIONS

This is a continuation-in-part application of my copending application Ser. No. 253,711, filed May 16, 1972, now abandoned; which in turn is a continuation-in-part application of application Ser. No. 85,733, filed Oct. 30, 1970, now abandoned; which in turn is a divisional application of application Ser. No. 738,379, filed June 17, 1968, now abandoned; which in turn is a continuation-in-part of application Ser. No. 649,812, filed June 29, 1967, now abandoned; which in turn is a continuation-in-part of application Ser. No. 409,563, filed Nov. 6, 1964, now abandoned.

DESCRIPTION OF THE INVENTION

This invention relates to the use of certain 2-aralkylimino-hexahydro-1-$R_1$-2H-azepines for their heart rate slowing activity. The azepines concerned with herein may be structurally represented by the formula:

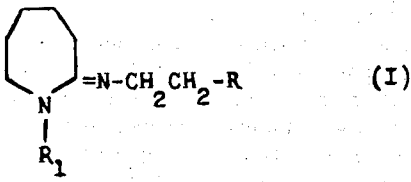

wherein R is a member selected from the group consisting of mono- and di-substituted phenyl wherein each substituent of said substituted phenyls is a member selected from the group consisting of loweralkyl and loweralkyloxy, and methylenedioxyphenyl, and $R_1$ is a member selected from the group consisting of hydrogen and loweralkyl. The pharmaceutically acceptable acid addition salts of (I) are also included within the scope of this invention.

As used herein "loweralkyl" may be a straight or branched chain and have from 1 to 8 carbon atoms, such as, for example, methyl, ethyl, propyl, isopropyl, butyl, tertbutyl, pentyl, hexyl, heptyl, octyl and the like, preferably methyl.

The subject compounds (I) have useful pharmacological properties which make them suitable for pharmaceutical applications. For example, a decrease in the heart rate has been found upon i.v. administration to anesthetized dogs without reducing cardiac output or the mechanical work of the heart at doses generally ranging from about 2.5 to about 20 mg/kg body weight.

In testing for cardiac slowing activity (reflexogenic sinus tachycardia), the following methodology is employed. A bilateral vagotomy is performed on the anesthetized dog [anesthesia consists of i.v. administration of thiopental sodium (20 mg/kg) maintained by subsequent i.v. injections of α-chloralose(60 mg/kg)]. Two doses of aminophylline (5 mg/kg i.v.) are administered at 15-minute intervals. The hypotensive effect of aminophylline activates the baro-receptors of the carotid sinus which, in turn, stimulates the sympathetic nervous system causing a reflex rise in the heart rate. Fifteen minutes after the second dose of aminophylline, the compound to be tested is administered i.v. and the effect on the heart rate is noted over a 30-minute period. Compounds showing heart-rate lowering activity of at least 18 sinus beats per minute for at least 5 minutes are considered to be active. Such compounds are useful in the treatment of angina pectoris since heart rate is considered to be a major determinant of myocardial oxygen consumption.

Certain of the azepines of formula (I) and their method of preparation are described in the literature. For example, in U.S. Pat. No. 3,378,438, certain of the subject compounds (wherein R is substituted phenyl and $R_1$ is hydrogen) are reported as antifungal agents.

The subject compounds may be prepared by reacting a fluoborate of formula (II), wherein $R_1$ is as previously defined, with a primary amine (III) having the formula $NH_2$—Z, wherein —Z stands for —$CH_2CH_2$—R with R being as previously defined. Stoichiometric quantities of reactants are preferably employed. The starting material (II) may be prepared according to Ber., 89, 2063 (1956). Suitable organic solvents for conducting the reaction include lower aliphatic alcohols, such as, for example, methanol, ethanol, 2-propanol, tert-butanol and the like; ethers, such as, for example, diethylether, tetrahydrofuran, dioxane and the like; lower halogenated hydrocarbons such as chloroform, methylene chloride, 1,2-dichloroethane and the like; and aromatic hydrocarbons such as benzene, toluene, xylene and the like. Elevated temperatures may be advantageously employed during the reaction. The resulting product (IV), in the form of the fluoborate salt, is converted to the corresponding base form (I) by conventional means, for example, by treatment with a suitable alkali such as alkali metal or alkaline earth metal hydroxides, carbonates and the like. The reactions may be illustrated as follows:

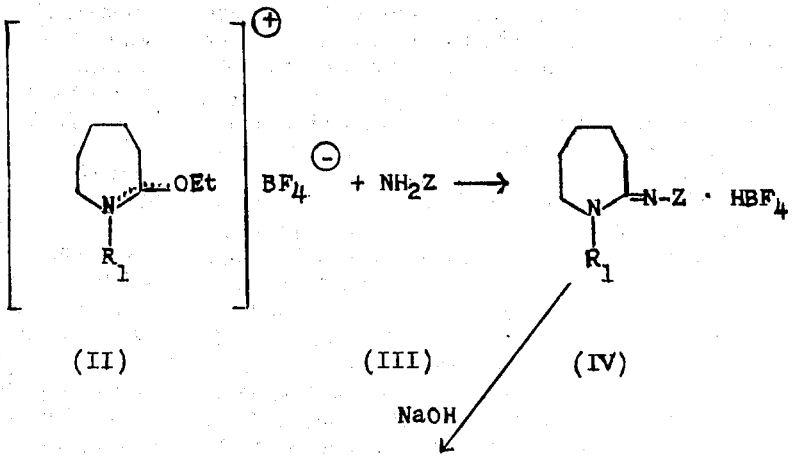

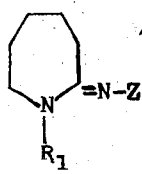

(I)

Alternatively, the subject compounds may be prepared by reacting an appropriate 1-loweralkyl-methyleneimine-2-one loweralkyl acetal [see Annalen, 641, 1 (1961) for the general method of preparing this type of starting material], an appropriate 1-$R_1$-2-loweralkylthiomethyleneiminium salt [see Annalen, 651, 89 (1962) for the general method of preparing this type of starting material], or the phosphorous oxychloride adduct or chloride prepared from an appropriate 1-$R_1$-methyleneiminine-2-one [see Berichte, 94, 2278 (1961) and Berichte, 96, 2671 (1963) for the general method of preparing these types of starting materials] with the primary amine (III) having the formula $NH_2$—Z. The reactants are preferably mixed in stoichiometric amounts, either without solvent if the amine is a liquid or with a suitable organic solvent. Elevated temperatures may be advantageously employed during these reactions. The products, when obtained as salts, may be converted to the corresponding base form (I) as described previously.

The subject compounds may be isolated as the free base or in the form of an acid addition salt by the synthetic process normally employed. These compounds, in base form, are convertible to therapeutically active non-toxic acid addition salts by treatment with an appropriate acid, such as, for example, an inorganic acid, such as, hydrohalic acid, e.g., hydrochloric, hydrobromic, hydroiodic acid; sulfuric or nitric acid; a phosphoric acid; an organic acid, such as, acetic, propionic, glycolic, lactic, pyruvic, malonic, succinic, maleic, fumaric, malic, tartaric, citric, benzoic, cinnamic, mandelic, methanesulfonic, p-toluenesulfonic, cyclohexanesulfamic, salicylic, p-aminosalicylic, 2-phenoxybenzoic, or 2-acetoxybenzoic acid. Conversely, the salt form can be converted in the usual manner into the free base.

In view of the cardiac slowing (anti-anginal) activity of the subject compounds (I), there is provided herein a method of treating patients with angina pectoris which comprises systemically administering to said patients an effective anti-anginal amount of said compounds, in base or acid addition salt form, preferably in admixture with a pharmaceutically acceptable carrier.

To prepare the pharmaceutical compositions of this invention, a 2-aralkylimino-hexahydro-1-$R_1$-2H-azepine (I) or salt thereof is combined as the active ingredient in intimate admixture with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carrier such as starches, sugars, diluents, granulating agents, lubricants, binders, disintegrating agents and the like in the case of oral solid preparations such as, for example, powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions herein will generally contain, per dosage unit, e.g., tablet, capsule, powder, injection, teaspoonful and the like, from about 5 to about 500 mg of the active ingredient, and, preferably, from about 10 to about 250 mg.

The following examples are intended to illustrate, but not to limit, the scope of the present invention.

EXAMPLE I

2-[($\beta$-3',4'-Dimethoxyphenethyl)imino]-hexahydro-1-methyl-2H-azepine perchlorate. Triethyloxonium fluoborate is prepared from 5.55 g. (0.06 mole) of epichlorohydrin and 11.25 g. (0.08 mole) of boron trifluoride etherate in ether. The salt is washed with ether by decantation and treated with a solution of 7.65 (0.06 mole) of N-methylcaprolactam in ether. After stirring at room temperature for three hours, the crystalline salt is washed with ether by decantation, dissolved in methylene chloride and treated with a methylene chloride solution of 9.06 g. (0.05 mole) of $\beta$-(3,4-dimethoxyphenyl)-ethylamine. After stirring at room temperature overnight, the reaction mixture is washed with dilute sodium hydroxide, dried and concentrated in vacuo, giving crude oily 2-[(3',4'-dimethoxyphenethyl)imino]-hexahydro-1-methyl-2H-azepine. An acid-base separation affords the base which is disstilled off (b.p. 180°–185°C./0.5 mm. Hg.). An acetone solution of the latter and an acetone solution of cyclohexanesulfamic acid are mixed together. The cyclohexanesulfamate salt of any residual phenethylamine precipitates and is removed. The mother liquor is concentrated and treated with sufficient 50% aqueous sodium hydroxide to convert the cyclohexanesulfamate salt back to the free base, which is extracted into methylene chloride. The methylene chloride solution is dried over anhydrous magnesium sulfate and then concentrated in vacuo. The residual oily base is then treated with an equivalent amount of perchloric acid in ethanol in the usual manner to yield the desired 2-[(β-3',4'-dimethoxyphenethyl)imino]-hexahydro-1-methyl-2H-azepine perchlorate, as crystals, m.p. 126°–130°C. Recrystallization from ethanol raises the m.p. to 130°–135°C.

EXAMPLE II

By repeating the procedure of Example I, except that an equivalent amount of an appropriate amine ($H_2N$—Z) and an equivalent amount of an appropriate N-alkyl-hexahydro-2H-azepine-2-one is used in place of N-methylcaprolactam, the following are obtained as respective products in the form of a perchlorate salt. Treatment with alkali affords the designated compound in base form.

2-[(β-4'-methylphenethyl)imino]-1-n-butyl-hexahydro-2H-azepine;

2-[(β-3',4'-methylenedioxyphenethyl)imino]-1-ethyl-hexahydro-2H-azepine;

2-[(β-3',4'-diethylphenethyl)imino]-1-methyl-hexahydro-2H-azepine; and

2-[(β-4'ethoxyphenethyl)imino]-1-ethyl-hexahydro-2H-azepine.

EXAMPLE III

By following the method of preparation described in U.S. Pat. No. 3,378,438, the following compounds are obtained:

2-[(β-3',4'-dimethoxyphenethyl)imino]-hexahydro-2H-azepine fumarate, m.p. 118°–19°C;

2-[(β-4'-methylphenethyl)imino]-hexahydro-2H-azepine hydrochloride;

2-[(β-3',4'-methylenedioxyphenethyl)imino]-hexahydro-2H-azepine; and

2-[(β-4'-ethylphenethyl)imino]-hexahydro-2H-azepine.

EXAMPLE IV — Capsules 10,000 Hard Gelatin capsules, each containing as the active ingredient (A.I.) 50 mg of 2-[(β-3',4'-dimethoxyphenethyl)imino]-hexahydro-1-methyl-2H-azepine perchlorate, are prepared from the following formulation:

|  | Grams |
|---|---|
| A.I. | 500 |
| Lactose | 750 |
| Starch | 250 |
| Talc | 250 |
| Calcium Stearate | 10 |

A uniform mixture of the active and supplementary ingredients is prepared and filled into two-piece hard gelatin capsules.

EXAMPLE V — Tablets 5,000 Compressed tablets, each containing as the active ingredient (A.I.) 10 mg of 2-[(β-3',4'-dimethoxyphenethyl)-imino]-hexahydro-2H-azepine fumarate, are prepared from the following formulation:

|  | Grams |
|---|---|
| A.I. | 50 |
| Starch | 75 |
| Dibasic Calcium phosphate, hydrous | 500 |
| Calcium Stearate | 2.5 |

The finely powdered ingredients are mixed well and are granulated with 10% starch paste. The granulation is dried and compressed into tablets using starch as the disintegrant and calcium stearate as the lubricant.

EXAMPLE VI — Injectable

The following formulation provides 1 liter of a parenteral suspension comprising 15 mg of 2-[(β-4'-methylphenethyl)imino]-hexahydro-2H-azepine as the active ingredient per milliliter:

|  | Grams |
|---|---|
| A.I. | 15.0 |
| Polysorbate 80 | 2.0 |
| Sodium chloride | 9.0 |
| Sodium Carboxymethyl cellulose | 10.0 |
| Methyl paraben | 1.8 |
| Propyl paraben | 0.2 |
| Water for Injection U.S.P., q.s. ad | 1 liter |

Dissolve the parabens, sodium chloride, and carboxymethyl cellulose in ½ the total volume of water by heating to 95°C to obtain a clear solution. Filter and autoclave. Dissolve the polysorbate in ⅓ the total volume of water. Filter and autoclave this second solution. Add sterile A.I. to the second solution and pass it through a sterile colloid mill. To the resulting suspension add the first solution with uniform stirring. Q.s. with sterilized water and stir while filling into sterile vials.

EXAMPLE VII — Oral Suspension

The following formulation provides 5 liters of an oral suspension comprising 100 mg of 2[(β-3',4'-methylenedioxyphenethyl)imino]-1-ethyl-hexahydro-2H-azepine as the active ingredient per teaspoonful (5 mls):

|  | Grams |
|---|---|
| A.I. | 100.0 |
| Sucrose | 300.0 |
| Dioctyl sodium sulfosuccinate | 0.5 |
| Bentonite | 22.5 |
| Methyl paraben | 7.5 |
| Propyl paraben | 1.5 |
| Antifoam A.F. Emulsion | 0.15 |
| Propylene glycol | 52.0 |
| FD&C Yellow No. 5 | 0.1 |
| Sodium cyclamate | 50.0 |
| Sodium saccharin | 5.0 |
| Orange flavor | 7.5 |
| Filtered purified water, q.s. ad 5 liters | |

Dissolve the parabens in the propylene glycol and add this solution to a solution of the sodium cyclamate, sodium saccharin and sucrose in half the water. Suspend the bentonite in hot (about 85°C) water and stir for 60 minutes. Add the bentonite solution to the former solution. Dissolve the sulfosuccinate in some water and suspend the A.I. in the resulting solution. Add the Antifoam A.F. Emulsion which has been diluted to a lotion consistency with a minimum amount of water and mix well. Add the latter suspension of A.I. to the former mixture and mix well. Add the FD&C Yellow No. 5 dissolved in a small amount of water. Add the orange flavor, q.s. to volume with water, and stir to a homogeneous mixture. Pass the mixture through a colloid mill and fill into suitable containers.

The foregoing pharmaceutical compositions are examples of unit dosages suitable for internal administration of the subject compounds (I) in base or acid addition salt form to man or other warm blooded animals for cardiac slowing (anti-anginal) activity.

The preferred compounds of formula (I) utilizable according to this invention are those wherein R is diloweralkyloxyphenyl. The most preferred species are:

a. 2-[(β-3′,4′-dimethoxyphenethyl)imino]-hexahydro-1-methyl-2H-azepine perchlorate, which has been found active in the previously described cardiac slowing test at doses of about 10 mg/kg i.v.; and b. 2-[(β-3′,4′-dimethoxyphenethyl)imino]-hexahydro-2H-azepine fumarate, which has been found active in said test at doses of about 5–10 mg/kg i.v.

What is claimed is:

1. A pharmaceutical composition in dosage unit form comprising per dosage unit from about 5 to about 500 mg of a member selected from the group consisting of a 2-aralkylimino-hexahydro-1-$R_1$-2H-azepine of the formula:

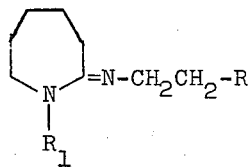

and a pharmaceutically acceptable acid addition salt thereof, wherein R is a member selected from the group consisting of mono- and di-substituted phenyl in which each substituent of said substituted phenyls is a member selected from the group consisting of loweralkyl and loweralkyloxy, and methylenedioxyphenyl, and $R_1$ is a member selected from the group consisting of hydrogen and loweralkyl, in admixture with a pharmaceutical carrier suitable for internal administration.

2. A solid pharmaceutical composition in dosage unit form comprising per dosage unit from about 5 to about 500 mg of a member selected from the group consisting of a 2-aralkylimino-hexahydro-1-$R_1$-2H-azepine of the formula:

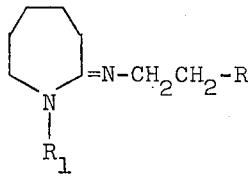

and a pharmaceutically acceptable acid addition salt thereof, wherein R is a member selected from the group consisting of mono- and di-substituted phenyl in which each substituent of said substituted phenyls is a member selected from the group consisting of loweralkyl and loweralkyloxy, and methylenedioxyphenyl, and $R_1$ is a member selected from the group consisting of hydrogen and loweralkyl, in admixture with a solid pharmaceutical carrier suitable for oral administration.

3. Claim 2 wherein said dosage unit is a tablet.

4. Claim 2 wherein said dosage unit is a capsule.

5. A solid pharmaceutical composition in dosage unit form comprising per dosage unit from about 5 to about 500 mg of a member selected from the group consisting of 2-[(β-3′,4′-dimethoxyphenethyl)imino]-hexahydro-1-methyl-2H-azepine and a pharmaceutically acceptable acid addition salt thereof in admixture with a solid pharmaceutical carrier suitable for oral administration.

6. A solid pharmaceutical composition in dosage unit form comprising per dosage unit from about 5 to about 500 mg of a member selected from the group consisting of 2-[(β-3′,4′-dimethoxyphenethyl)imino]-hexahydro-2H-azepine and a pharmaceutically acceptable acid addition salt thereof in admixture with a solid pharmaceutical carrier suitable for oral administration.

7. A liquid pharmaceutical composition in dosage unit form comprising per dosage unit from about 5 to about 500 mg of a member selected from the group consisting of a 2-aralkylimino-hexahydro-1-$R_1$-2H-azepine of the formula:

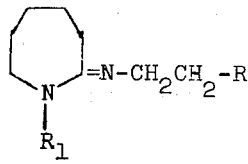

and a pharmaceutically acceptable acid addition salt thereof, wherein R is a member selected from the group consisting of mono and di-substituted phenyl in which each substituent of said substituted phenyls is a member selected from the group consisting of loweralkyl and loweralkyloxy, and methylenedioxyphenyl, and $R_1$ is a member selected from the group consisting of hydrogen and loweralkyl, in a liquid medium suitable for oral administration.

8. A liquid pharmaceutical composition in dosage unit form comprising per dosage unit from about 5 to about 500 mg of a member selected from the group consisting of 2-[(β-3′,4′-dimethoxyphenethyl)imino]-hexahydro-1-methyl-2H-azepine and a pharmaceutically acceptable acid addition salt thereof in a liquid medium suitable for oral administration.

9. A liquid pharmaceutical composition in dosage unit form comprising per dosage unit from about 5 to about 500 mg of a member selected from the group consisting of 2-[(β-3′,4′-dimethoxyphenethyl)imino]-hexahydro-2H-azepine and a pharmaceutically acceptable acid addition salt thereof in a liquid medium suitable for oral administration.

10. An injectable pharmaceutical composition in dosage unit form comprising per dosage unit from about 5 to about 500 mg of a member selected from the group consisting of a 2-aralkylimino-hexahydro-1-$R_1$-2H-azepine of the formula:

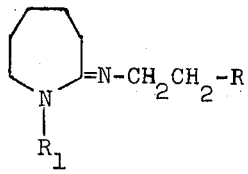

and a pharmaceutically acceptable acid addition salt thereof, wherein R is a member selected from the group consisting of mono- and di-substituted phenyl in which each substituent of said substituted phenyls is a member selected from the group consisting of loweralkyl and loweralkyloxy, and methylenedioxyphenyl, and $R_1$ is a member selected from the group consisting of hydrogen and loweralkyl, in a sterile medium suitable for parenteral administration.

11. An injectable pharmaceutical composition in dosage unit form comprising per dosage unit from about 5 to about 500 mg of a member selected from the group consisting of 2-[(β-3′,4′-dimethoxyphenethyl)imino]-hexahydro-1-methyl-2H-azepine and a pharmaceutically acceptable acid addition salt thereof in a sterile medium suitable for parenteral administration.

12. An injectable pharmaceutical composition in dosage unit form comprising per dosage unit from about 5 to about 500 mg of a member selected from the group consisting of 2-[(β-3′,4′-dimethoxyphenethyl)imino]-hexahydro-2H-azepine and a pharmaceutically acceptable acid addition salt thereof in a sterile medium suitable for parenteral administration.

13. The method of treating a warm blooded animal having angina pectoris which comprises systemically administering to said warm blooded animal an effective anti-anginal amount of a member selected from the group consisting of a 2-aralkylimino-hexahydro-1-$R_1$-2H-azepine of the formula:

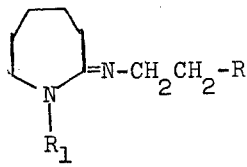

and a pharmaceutically acceptable acid addition salt thereof, wherein R is a member selected from the group consisting of mono- and di-substituted phenyl, each substituent of said substituted phenyls being a member selected from the group consisting of loweralkyl and loweralkyloxy, and methylenedioxyphenyl, and $R_1$ is a member selected from the group consisting of hydrogen and loweralkyl, in admixture with a pharmaceutical carrier suitable for internal administration.

14. The method of treating a warm blooded animal having angina pectoris which comprises systemically administering to said warm blooded animal a pharmaceutical composition in dosage unit form comprising per dosage unit from about 5 to about 500 mg of a member selected from the group consisting of a 2-aralkylimino-hexahydro-1-$R_1$-2H-azepine of the formula:

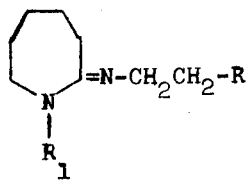

and a pharmaceutically acceptable acid addition salt thereof, wherein R is a member selected from the group consisting of mono- and di-substituted phenyl, each substituent of said substituted phenyls being a member selected from the group consisting of loweralkyl and loweralkyloxy, and methylenedioxyphenyl, and $R_1$ is a member selected from the group consisting of hydrogen and loweralkyl, in admixture with a pharmaceutical carrier suitable for internal administration.

15. The method of treating a warm blooded animal having angina pectoris which comprises systemically administering to said warm blooded animal a solid pharmaceutical composition in dosage unit form comprising per dosage unit from about 5 to about 500 mg of a member selected from the group consisting of 2-[(β-3′,4′-dimethoxyphenethyl)imino]-hexahydro-1-methyl-2H-azepine and a pharmaceutically acceptable acid addition salt thereof in admixture with a solid pharmaceutical carrier suitable for oral administration.

16. The method of treating a warm blooded animal having angina pectoris which comprises systemically administering to said warm blooded animal a solid pharmaceutical composition in dosage unit form comprising per dosage unit from about 5 to about 500 mg of a member selected from the group consisting of 2-[(β-3′,4′-dimethoxyphenethyl)imino]-hexahydro-2H-azepine and a pharmaceutically acceptable acid addition salt thereof in admixture with a solid pharmaceutical carrier suitable for oral administration.

17. The method of treating a warm blooded animal having angina pectoris which comprises systemically administering to said warm blooded animal a liquid pharmaceutical composition in dosage unit form comprising per dosage unit from about 5 to about 500 mg of a member selected from the group consisting of a 2-aralkylimino-hexahydro-1-$R_1$-2H-azepine of the formula:

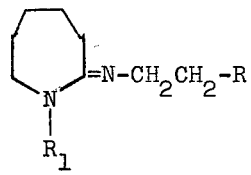

and a pharmaceutically acceptable acid addition salt thereof, wherein R is a member selected from the group consisting of mono- and di-substituted phenyl, each substituent of said substituted phenyls being a member selected from the group consisting of loweralkyl and loweralkyloxy, and methylenedioxyphenyl, and $R_1$ is a member selected from the group consisting of hydrogen and loweralkyl, in a liquid medium suitable for oral administration.

18. The method of treating a warm blooded animal having angina pectoris which comprises systemically administering to said warm blooded animal a liquid pharmaceutical composition in dosage unit form comprising per dosage unit from about 5 to about 500 mg of a selected from the group consisting of 2-[(β-3′,4′-dimethoxyphenethyl)imino]-hexahydro-1-methyl-2H-azepine and a pharmaceutically acceptable acid addition salt thereof in a liquid medium suitable for oral administration.

19. The method of treating a warm blooded animal having angina pectoris which comprises systemically administering to said warm blooded animal a liquid pharmaceutical composition in dosage unit form comprising per dosage unit from about 5 to about 500 mg of a member selected from the group consisting of 2-[(β-3′,4′-dimethoxyphenethyl)imino]-hexahydro-2H-azepine and a pharmaceutically acceptable acid addition salt thereof in a liquid medium suitable for oral administration.

20. The method of treating a warm blooded animal having angina pectoris which comprises systemically administering to said warm blooded animal an injectable pharmaceutical composition in dosage unit form comprising per dosage unit from about 5 to about 500 mg of a member selected from the group consisting of a 2-aralkylimino-hexahydro-1-$R_1$-2H-azepine of the formula:

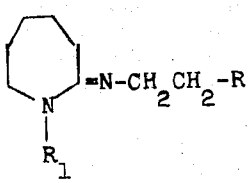

and a pharmaceutically acceptable acid addition salt thereof, wherein R is a member selected from the group consisting of mono- and di-substituted phenyl each substituent of said substituted phenyls being a member selected from the group consisting of loweralkyl and loweralkyloxy, and methylenedioxyphenyl, and $R_1$ is a member selected from the group consisting of hydrogen and loweralkyl, in a sterile medium suitable for parenteral administration.

21. The method of treating a warm blooded animal having angina pectoris which comprises systemically administering to said warm blooded animal an injectable pharmaceutical composition in dosage form comprising per dosage unit from about 5 to about 500 mg of a member selected from the group consisting of 2-[($\beta$-3′,4′-dimethoxyphenethyl)imino]-hexahydro-1-methyl-2H-azepine and a pharmaceutically acceptable acid addition salt thereof in a sterile medium suitable for parenteral administration.

22. The method of treating a warm blooded animal having angina pectoris which comprises systemically administering to said warm blooded animal an injectable pharmaceutical composition in dosage unit form comprising per dosage unit from about 5 to about 500 mg of a member selected from the group consisting of 2-[($\beta$-3′,4′-dimethoxyphenethyl)imino]-hexahydro-2H-azepine and a pharmaceutically acceptable acid addition salt thereof in a sterile medium suitable for parenteral administration.

* * * * *

UNITED STATES PATENT AND TRADEMARK OFFICE
CERTIFICATE OF CORRECTION

PATENT NO. : 3,959,479
DATED : May 25, 1976
INVENTOR(S) : Poos, George Ireland

It is certified that error appears in the above-identified patent and that said Letters Patent are hereby corrected as shown below:

In Column 4, line 56, the word "disstilled" should read --- distilled ---.

In Column 10, line 46, the word "of a selected from" should read --- of a member selected from ---.

Signed and Sealed this

Twenty-eighth Day of June 1977

[SEAL]

Attest:

RUTH C. MASON
*Attesting Officer*

C. MARSHALL DANN
*Commissioner of Patents and Trademarks*